(12) United States Patent
Tindall

(10) Patent No.: US 9,820,679 B2
(45) Date of Patent: Nov. 21, 2017

(54) CANINE LEG MEASUREMENT DEVICE AND METHOD OF USE

(76) Inventor: Eric Paul Tindall, Oxford, MI (US)

( * ) Notice: Subject to any disclaimer, the term of this patent is extended or adjusted under 35 U.S.C. 154(b) by 0 days.

(21) Appl. No.: 11/787,507

(22) Filed: Apr. 16, 2007

(65) Prior Publication Data

US 2007/0245583 A1    Oct. 25, 2007

Related U.S. Application Data

(60) Provisional application No. 60/745,331, filed on Apr. 21, 2006.

(51) Int. Cl.
*A61B 5/107* (2006.01)
*A61B 5/00* (2006.01)

(52) U.S. Cl.
CPC .......... *A61B 5/1072* (2013.01); *A61B 5/4504* (2013.01); *A61B 5/4528* (2013.01); *A61B 2503/40* (2013.01)

(58) Field of Classification Search
CPC .......................... A61B 5/1072; A61B 2503/40
USPC ...... 33/511, 485, 494, 832, 833, 464, 679.1, 33/512
See application file for complete search history.

(56) References Cited

U.S. PATENT DOCUMENTS

| 325,134 | A |   | 8/1885  | Wainwright |            |
|---------|---|---|---------|------------|------------|
| 721,800 | A |   | 3/1903  | Heatly     |            |
| 1,035,033 | A | * | 8/1912 | Nelson ............................. | 33/464 |
| D177,541 | S |   | 4/1956  | Wambach    |            |
| 2,979,825 | A | * | 4/1961 | Westbrook .................... | 33/679.1 |
| 3,895,356 | A | * | 7/1975 | Kraus ........................... | 702/161 |
| 3,943,630 | A |   | 3/1976 | Hildebrand |            |
| 4,037,327 | A |   | 7/1977 | Hildebrand |            |
| 4,407,070 | A | * | 10/1983 | Lowe ............................. | 33/511 |
| 4,823,469 | A | * | 4/1989 | Broselow ....................... | 33/760 |
| 5,010,656 | A | * | 4/1991 | Broselow ....................... | 33/759 |
| 5,761,819 | A | * | 6/1998 | Ledy-Gurren ................. | 33/501 |
| 5,974,678 | A | * | 11/1999 | Landauer ....................... | 33/512 |
| 6,128,824 | A | * | 10/2000 | Yang ............................. | 33/511 |
| 6,446,351 | B1 | * | 9/2002 | Zhang et al. ................... | 33/832 |

(Continued)

OTHER PUBLICATIONS

"E-Z Wicket—Adjustable Measuring Wickets" from www.ezwicket.com, Apr. 11, 2007, 3 pages, Internet, US.

(Continued)

*Primary Examiner* — Christopher Fulton
(74) *Attorney, Agent, or Firm* — Richard A. Ryan

(57) ABSTRACT

A measurement device and method for measuring a portion of an animal's leg to more accurately and fairly determine the height setting required for a jump apparatus to be jumped by the animal. The device, which is particularly useful for measuring dogs for Flyball competitions, comprises an elongated body member and a sliding mechanism slidably attached thereto. The preferred body member has a curved cross-section. A preferred sliding mechanism comprises a slot disposed in the body member and a slide member that slidably engages the slot. In use, the body member is placed against the ulna of the dog's front leg with the first end of the body member positioned at the intersection of the ulna and the accessory carpal bone so a contact plate of the slide member can be slid against the elbow. A color coded and labeled chart on the body member provides the jump height setting.

18 Claims, 5 Drawing Sheets

(56) References Cited

U.S. PATENT DOCUMENTS 6,647,635 B1 * 11/2003 Banfield .......................... 33/511

OTHER PUBLICATIONS

"Everything Sheltie—ProAdvantage Steel Wicket" from www.everythingsheltie.com/wicket.htm, Apr. 11, 2007, 2 pages, Internet, US.

"Light weight / Folding Measuring Device (Wicket)" from www.starsandstripesagility.com, 3 pages, Internet, US.

* cited by examiner

| Elbow to Accessory Carpal Bone Measurement | Jump Height |
|---|---|
| Up to 4.5" | 6" |
| Over 4.5" up to 5" | 7" |
| Over 5" up to 5.5" | 8" |
| Over 5.5" up to 6" | 9" |
| Over 6" up to 6.5" | 10" |
| Over 6.5" up to 7" | 11" |
| Over 7" | 12" |

CANINE LEG MEASUREMENT DEVICE AND METHOD OF USE

CROSS-REFERENCE TO RELATED APPLICATIONS

This application claims the benefit of U.S. Provisional Patent Application No. 60/745,331 filed on Apr. 21, 2006.

BACKGROUND OF THE INVENTION

A. Field of the Invention

The field of the present invention relates generally to devices for measuring the length of an object and methods of using the measuring device to accomplish the measurement objective. More particularly, the present invention relates to such devices and methods that are specifically configured to measure a portion of the leg of an animal. Even more particularly the present invention relates to such devices and methods that are useful for measuring a portion of the leg of a dog for the purpose of establishing a jump height in a competitive race, such as a Flyball competition.

B. Background

Many competitive sporting events pertain to the relative performance of one or more animals, including various horse and dog racing competitions, in which one animal competes against other animals to run a specified distance in the fastest time. A very popular dog racing sport is commonly known as Flyball, which is a relay type of race competition in which one team of dogs competes against another team of dogs. In the typical Flyball race, two teams of four dogs each race side-by-side over a course of a specified length while jumping over a plurality of hurdles along the course and retrieving a ball from one end of the course. Official Flyball competitions require each dog in the team to race, one at a time in a relay fashion, down a fifty-one foot course while jumping over four spaced apart hurdles of a specified height, retrieve a ball from a box-like device, commonly referred to as a flyball box, and then return the ball to the beginning of the course where the next dog then performs the same tasks. The flyball box is configured such that the dog must step on a large pedal-like device to activate the release of the ball, which is typically a tennis ball, that the dog catches or otherwise retrieves. Once all four dogs on a team have correctly completed the course, the team has finished the race and the fastest team is declared the winner of the race.

The two primary Flyball sanctioning organizations in the United States, which are United Flyball League International (U-FLI, the assignee of the present invention) and North American Flyball Association (NAFA), allow any dog of any size or breed, including mix breeds, to compete in their sanctioned Flyball competitions. Because part of the race involves jumping over hurdles along the course and different dogs are of different heights, which tends to give a jumping advantage to a taller dog (though not always true), the rules are configured such that the size of the smallest dog in a team sets the height of the hurdles for all of the dogs in that team. Based on a measured size of the smallest dog, which is intended to reflect its jump height, the height of the hurdles is determined from a chart or other mechanism so that a certain size dog will always have to jump a certain height of hurdle.

To provide a consistent course from one tournament or other type of competition to another so that individual and/or dog teams and their competitive times can be compared, it was necessary to develop a uniform manner in which to measure the dog for setting the height of the hurdles. Ideally, the selected form of measurement would correspond, at least generally, to the ability of the dog to jump. The standard method of measuring dogs for determining the height of the hurdles for Flyball purposes is to determine the dog's wither height using a wicket type of measuring device. This same type of device is utilized in other dog sports, including but not limited to Agility competitions, which is another dog sport where a handler directs a dog through an obstacle course for time and accuracy, and in Conformation shows, in which judges evaluate a dog for how well it conforms to published breed standards. The measurement of the dog's withers is the distance from the ground to the highest point of its back at the shoulders. The withers measurement is made to the ridge that is located between the shoulder blades just behind the base of the dog's neck. To obtain an accurate wither height, the dog should be measured standing on a hard, level surface with the front legs vertical and the head in its natural position. Though not that consistently accurate, one way to measure the withers height is to tape a yardstick to a vertical surface, such as a wall, place one edge of a ruler or triangle against the yardstick so that it extends outward from the yardstick and then slide the ruler/triangle down the yardstick until it rests on the dog's withers. The point on the yardstick at the bottom of the ruler or triangle will be the withers height.

For purposes of dog competitions, it is necessary to have a more consistent and accurate method of determining withers height so that dogs can be fairly compared, as in Conformation shows, or the course can be properly adjusted, as in Flyball or Agility competitions. Over the years, various wicket type of measuring devices have been developed to measure the withers height of a dog or other animal. For instance, U.S. Pat. No. 325,134 to Wainwright and U.S. Pat. No. 721,800 to Heatly describe height measuring devices that are of the type having a freely upstanding measuring stick with an arm cantilevered therefrom that rests on the point to be measured, which are devices generally similar to the yardstick method set forth above. The Wainwright patent describes the device being used to measure the wither height of a horse. U.S. Pat. Nos. 3,943,630 and 4,037,327, both to Hildebrand, describe dog height measuring wickets that comprise a U-shaped member having a pair of spaced apart tubular legs, an interconnecting bar at the top of the legs, a cross bar connecting the legs below the interconnecting bar and mechanisms for adjusting and indicating the height of the cross bar. In use, the person using the wicket slips the device over the dog's shoulders, places the wicket's feet on the floor and determines whether the dog's shoulder height is below the preset height of the cross bar or not. A number of devices at least generally similar to the patented devices described above are presently commercially available.

Once the withers height of the dog is determined, this information is utilized to adjust the height of the hurdles or other jump devices. In Flyball, for instance, certain organizations utilize the wither height to directly calculate the height of the hurdles which the dogs must jump over as they run the required course. As an example, under current NAFA rules the hurdle height is set at four inches (10 cm) below the withers height of the smallest dog, with the minimum hurdle height being seven inches (20.3 cm) and the maximum hurdle height being fourteen inches (40.6 cm).

Although measuring the withers height of a dog with a wicket is the currently accepted and sanctioned height measurement for all competitive dog sports, including Flyball, this method and the available devices have well known limitations. One such limitation is that the wither height can be substantially affected by varying stances or foot placement by the dog and/or its handler that results in the shoulder blades being raised or lowered. Unfortunately, the varied stance or foot placement creates an inconsistent procedure of accurate wither measurement that can result in a one to two inch jump height variance for an individual dog. The time that it takes to position the dog in the correct stance and the length of time that the dog must remain stationary in that position often results in high stress levels for the dog, its handler and the judge conducting the wither height measurement. Another problem is that because the wicket method of measurement measures from the ground to the withers it includes the height of the dog's body, which generally results in heavy bodied dogs receiving higher jump measurements. As a result of the higher jump measurements, the heavy bodied dogs must jump disproportionately higher jump heights. As well known, this can negatively impact these longevity of these dogs in performance events, such as Flyball and the like.

In addition to the foregoing, most wicket devices are not that easy or quick to use. For instance, most such devices require additional tools, such as pliers and a level, to adjust and the device must be leveled and/or calibrated before use. The floor or other surface on which the dog and the wicket stands must be level, something that is not always possible. Further, most wickets are relatively heavy and awkward (due to their dimensions) to carry, making them difficult to transport. This is a particular problem for flying when the wicket must fit into a standard suitcase or require special packaging.

What is needed, therefore, is an improved measurement device and method for measuring the relative jump height capability of related animals so that these measurements can be utilized to set the height levels of apparatuses to be jumped. The preferred measurement device should be easy to utilize and configured to obtain consistent, repeatable measurements that can be generally correlated to the animal's jumping ability. Preferably, the measurement device will be suitable for hand-held use, easy to transport and relatively inexpensive to manufacture. The preferred measurement device should remove the various variables associated with presently configured devices for measuring the wither height of the animal. The preferred method of use should reduce the amount of time and variances that are associated with present methods of determining the animal's relative jumping ability. Preferably, an improved method of use will allow a person to quickly and accurately correlate a measured length on the animal to the height of which an apparatus should be set for the animal to jump over.

SUMMARY OF THE INVENTION

The canine leg measurement device and method of use of the present invention solves the problems and provides the benefits identified above. That is to say, the present invention discloses a canine leg measurement device that measures a portion of the dog's leg to determine the relative jump height capability of the dog for purpose of setting the height levels of apparatuses that the dog will jump, such as the height of hurdles in a Flyball race. In a preferred embodiment of the present invention, the canine leg measurement device is configured as a hand-held caliper type of device that is easy to use and able to obtain consistent, repeatable leg measurements without requiring the dog or its handler to assume a particular stance or position for an extended period of time. The preferred embodiment of the canine leg measurement device and method of its use allows the user to correlate the measured length of a portion of the dog's front leg to a setting for the jump height of one or more jumping apparatuses, such as hurdles. In a preferred embodiment, the canine measurement device is easy to transport and relatively inexpensive to manufacture.

In one general aspect of the present invention, the canine leg measurement device for measuring a portion of a dog's leg to determine a jump height setting comprises an elongated body member, a sliding mechanism that is slidably attached to the body member and at least one measurement chart on the body member. The body member has a first end, a second end, an upper surface and a lower surface. In the preferred embodiment, the body member has a generally curved cross-section and a tip with an outwardly extending end at the first end of the body member. A preferred sliding mechanism comprises an elongated slot disposed in the body member and a slide member that slidably engages the slot to move along the body member. Preferably, the measurement chart is on the upper surface and is configured to allow the user to directly read the required jump height setting. The leg measurement device measures the distance between the dog's accessory carpal bone and the elbow of one of its front legs to provide the desired jump height setting when the upper surface of the body member is placed against the ulna of the leg, the tip engages the leg at the intersection of the ulna and the accessory carpal bone and the sliding mechanism abuts the elbow. Preferably, the outwardly extending end of the tip is shaped and configured to abut the leg. In a preferred embodiment, the sliding mechanism further comprises one or more fasteners that are configured to slidably attach the slide member to the body member through the slot and the slide member has a contact plate that abuts the elbow, a push plate that the user pushes on to move the slide member and a base member interconnecting the contact plate and the push plate, with the base member configured to slide in relation to the upper surface of the body member.

In a preferred method of using the leg measurement device of the present invention measure the leg of an animal to determine a jump height setting, the user first positions the animal with the leg presented and the paw relaxed. Then the user supports the ulna of the animal's front leg against the upper surface of the body member of the leg measurement device. In the preferred embodiment of the leg measurement device, the portion of the front leg is cradled in the curved upper surface of the body member. Then the user places the tip at the first end of the body member against the intersection of the ulna and the accessory carpal bone of the front leg. The user then slides the slide member toward the first end of the body member until it abuts the elbow of the front leg, thereby essentially measuring the ulna portion of the animal's front leg. Once the slide member is in position, the user then reads the measurement chart, which is preferably on the upper surface of the body member, at the position where the slide member abuts the elbow. In one embodiment, this can be the length of the ulna in inches or centimeters/millimeters. In the preferred embodiment, however, the measurement chart directly indicates the jump height setting so no additional calculation or determination is required.

Accordingly, the primary objective of the present invention is to provide an animal leg measurement device and method of use that provides the advantages discussed above and overcomes the disadvantages and limitations associated with presently available devices for measuring the withers height of an animal for purposes of setting the height of one or more jump apparatuses.

It is also an important object of the present invention to provide an animal leg measurement device that is easy to utilize, does not require the animal to be in a particular stance for an extended length of time and is able to obtain consistent, repeatable measurements of a portion of the animal's leg.

It is also an important object of the present invention to provide an animal leg measurement device and method of use that is particularly configured to measure a portion of the front leg of a dog for purposes of correlating that length measurement to a height setting for a jump apparatus in a dog competition such as Flyball.

It is also an important object of the present invention to provide a canine leg measurement device and method of use that is a hand-held caliper type device which measures the portion of a dog's front leg between the elbow and the Accessory Carpal Bone (Pisiform) for determining the height setting for a jump apparatus from a jump height scale associated with the leg measurement device.

It is also an important object of the present invention to provide a method of determining a jump height setting that includes the steps of measuring a portion of an animal's leg and correlating that measurement to the height setting for a jump apparatus.

It is also an important object of the present invention to provide a method of determining a jump height setting for a dog that includes the steps of measuring a portion of the dog's front leg with a canine leg measurement device and correlating the measured length to a chart indicating the height setting for a jump apparatus, such as a hurdle used in a Flyball competition.

It is also an object of the present invention to a canine leg measurement device that is easy to transport and relatively inexpensive to manufacture.

The above and other objectives of the present invention will be explained in greater detail by reference to the attached figures and the description of the preferred embodiment which follows. As set forth herein, the present invention resides in the novel features of form, construction, mode of operation and combination of processes presently described and understood by the claims.

BRIEF DESCRIPTION OF THE DRAWINGS

In the drawings which illustrate the preferred embodiments and the best modes presently contemplated for carrying out the present invention.

DETAILED DESCRIPTION OF THE PREFERRED EMBODIMENTS

With reference to the figures where like elements have been given like numerical designations to facilitate the reader's understanding of the present invention, the preferred embodiments of the present invention are set forth below. The enclosed figures and drawings are merely illustrative of a preferred embodiment and represents one of several different ways of configuring the present invention. Although specific components, materials, configurations and uses are illustrated, it should be understood that a number of variations to the components and to the configuration of those components described herein and in the accompanying figures can be made without changing the scope and function of the invention set forth herein. For instance, although the figures and description provided herein are primarily described as being utilized to measure a portion of the front leg of a dog for a jump height setting, those skilled in the art will readily understand that this is merely for purposes of simplifying the present disclosure and that the present invention is not so limited. For instance, the present invention may be equally applicable for use with the rear leg of a dog, with other animals and for other purposes (i.e., Conformation shows).

Figure 5:
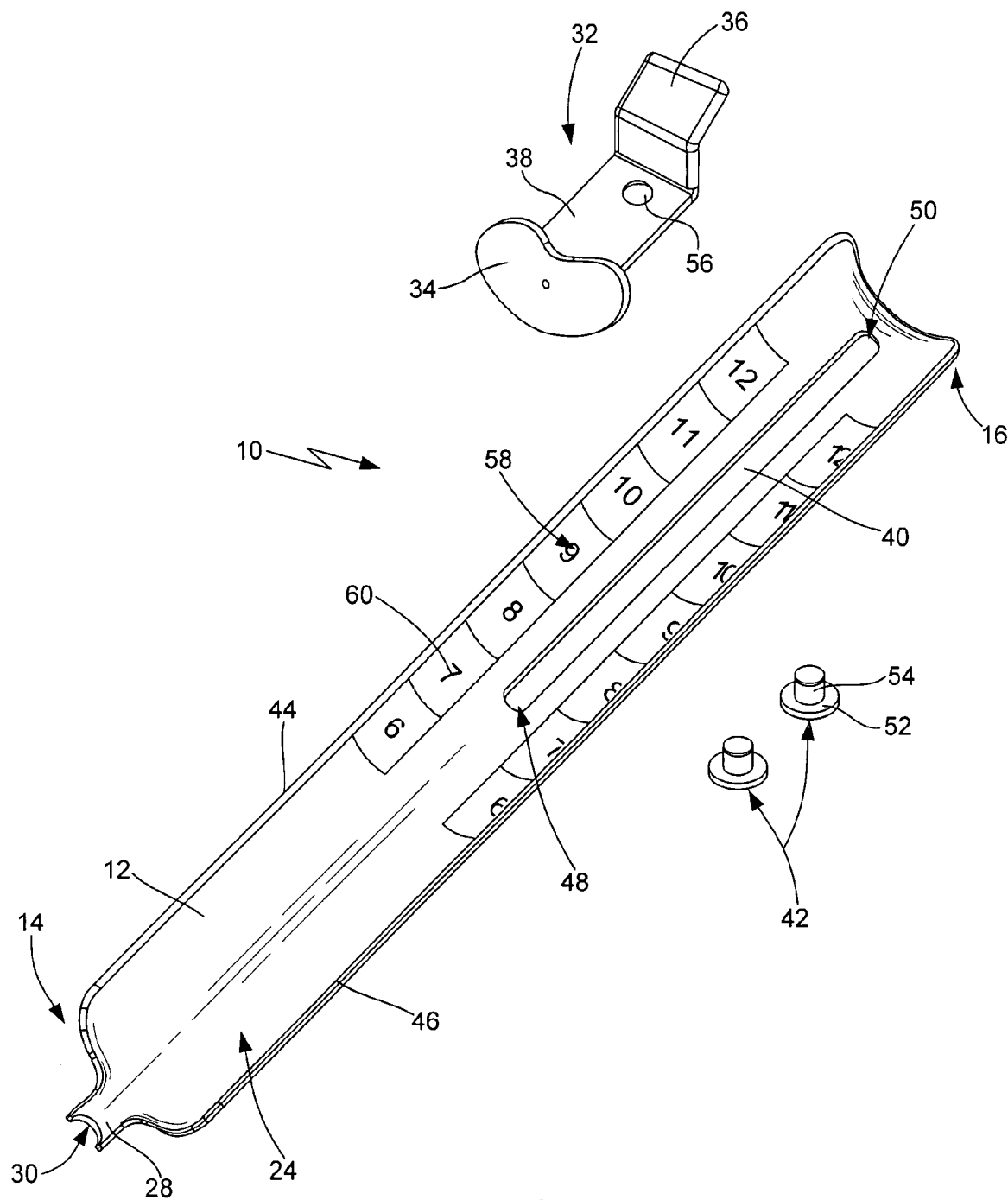
FIG. 5 is an exploded top perspective view of the leg measurement device of FIG. 1.
Figure 6:
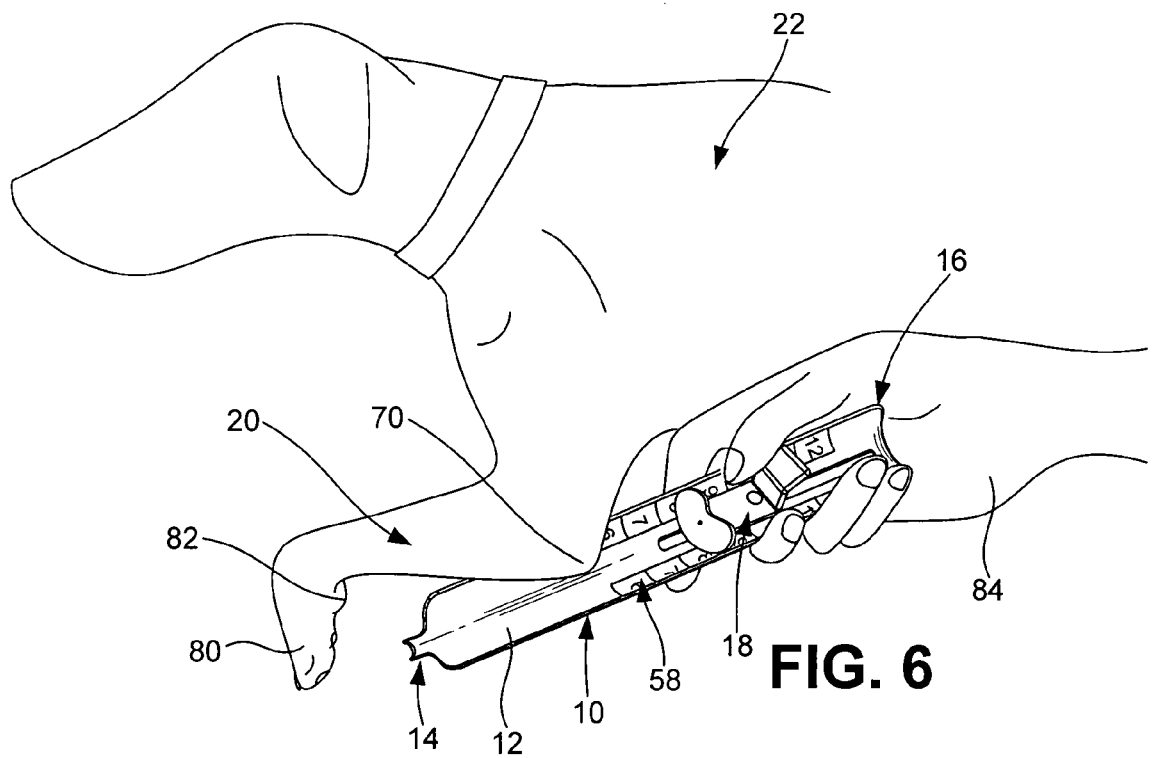
FIG. 6 is a side view of a canine leg measurement device configured according to the preferred embodiment of the present invention being shown being readied for use to measure a dog with its front leg in a relaxed position.
Figure 7:
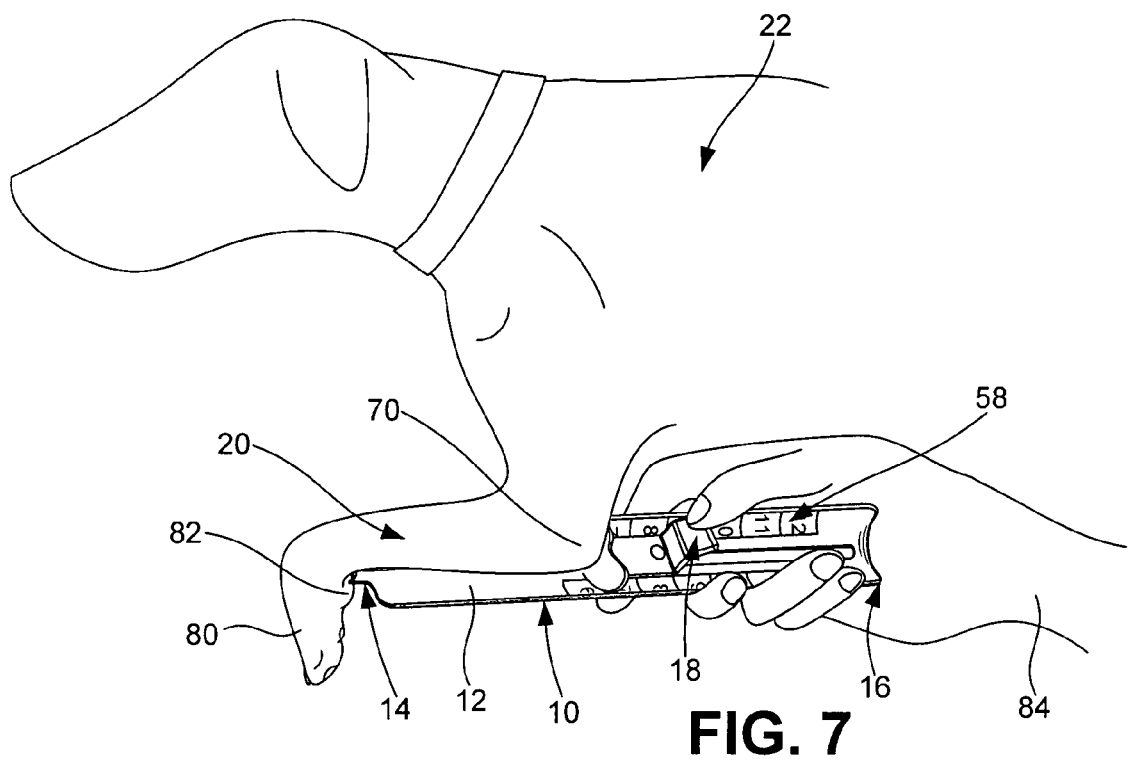
FIG. 7 is a side view of the canine leg measurement device of FIG. 6 shown in use to measure a portion of the front leg of the dog.

A canine leg measurement device that is manufactured out of the components and configured pursuant to a preferred embodiment of the present invention is shown generally as 10 in FIGS. 1 through 7. In the embodiment shown in the figures, leg measurement device 10 generally comprises a body member 12, having a first end 14 and a second end 16, and a sliding mechanism 18 that slidably is attached to body member 12. As explained in more detail below and shown in FIGS. 6 and 7, in the preferred embodiment of the present invention the leg measurement device 10 is utilized to measure a portion of the front leg 20 of a dog 22. As shown in FIGS. 1 through 7, body member 12 is generally elongated to correspond to the length of the portion of the front leg 20 to be measured and has a curved, arched or half-round cross-section to facilitate its placement against front leg 20. Body member 12 can be made out of a wide variety of different materials, including metals, plastics, wood, composites and combinations of materials. Preferably, the material chosen for body member 12 is lightweight for ease of use and transport, relatively strong so it does not easily break during use or transport and sufficiently rigid so that it can be placed and held in an abutting relationship against the front leg 20 of dog 22 to obtain the desired measurement. In one preferred configuration, body member 12 is made out of aluminum. Except for the upwardly protruding sliding mechanism 18, it is preferred that the upper surface 24 and lower surface 26 of body member 12 be generally smooth as upper surface 24 will be held against the front leg 20 of dog 22 and lower surface 26 will be held by the user during a preferred use of leg measurement device 10, as shown in FIGS. 6 and 7.

In the preferred embodiment, the first end 14 of body member 12 is provided with a tip 28 that is shaped and configured to beneficially engage a portion of the front leg 20 of dog 22, as shown in FIG. 7 and explained in more detail below. In the preferred configuration, tip 28 extends outwardly from first end 14 of body member 12 with its outwardly extending end 30 being generally curved or arched shaped to facilitate being placed in abutting relation against the desired portion of front leg 20. As explained below, with tip 28 extending outwardly from first end 14 and its outwardly extending end 30 being curved, it will be easier for the user to accurately obtain the desired measurement. If desired, all or a portion of tip 28 can be coated with a material to "soften" the contact with the dog 22 during the measurement process.

Figure 1:
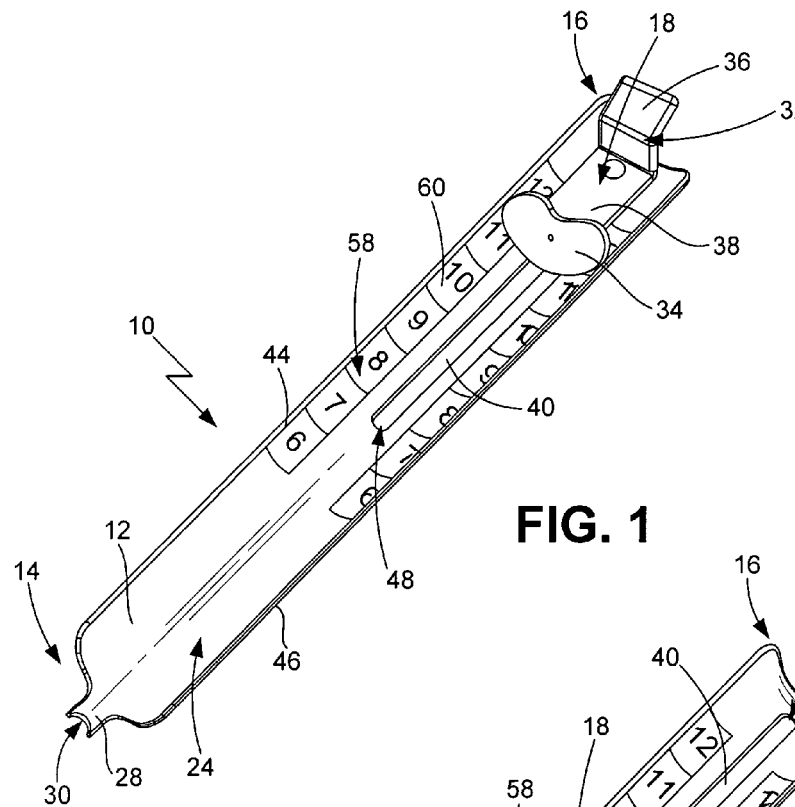
FIG. 1 is a top perspective view of a canine measurement leg device configured according to a preferred embodiment of the present invention showing the sliding mechanism in its maximum position.
Figure 2:
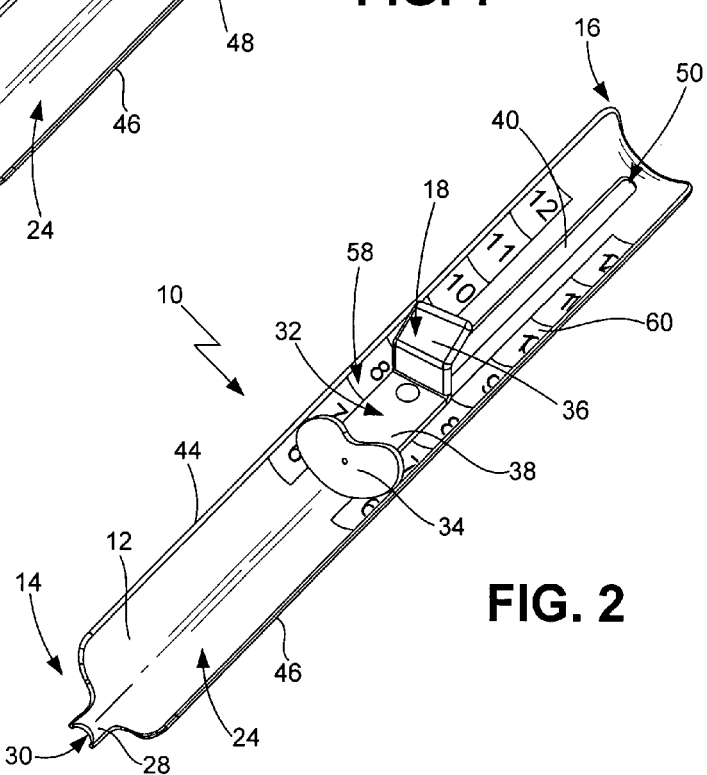
FIG. 2 is a top perspective view of the canine leg measurement device of FIG. 1 shown with the sliding mechanism in its minimum position.
Figure 3:
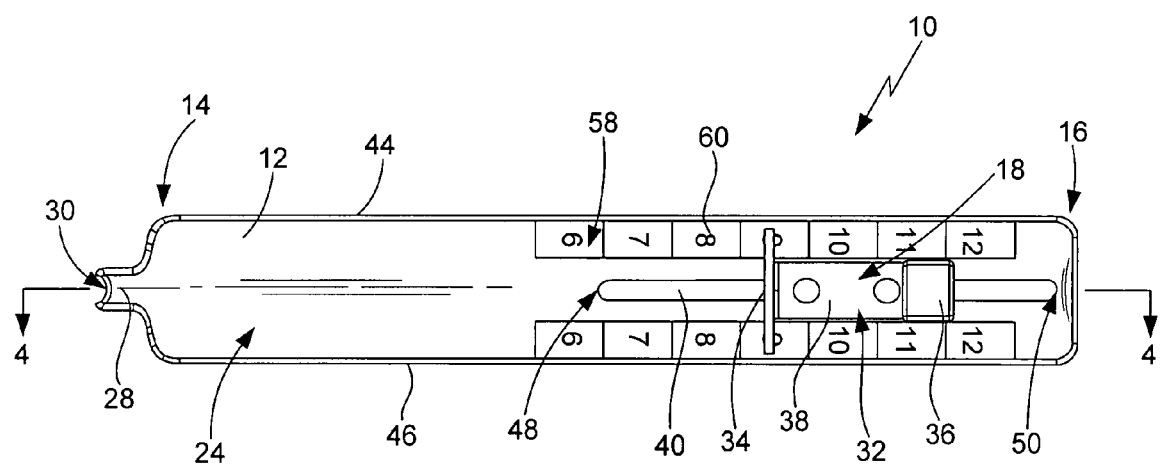
FIG. 3 is a top view of the canine leg measurement device of FIG. 1 shown with the sliding mechanism it an intermediate position.
Figure 4:
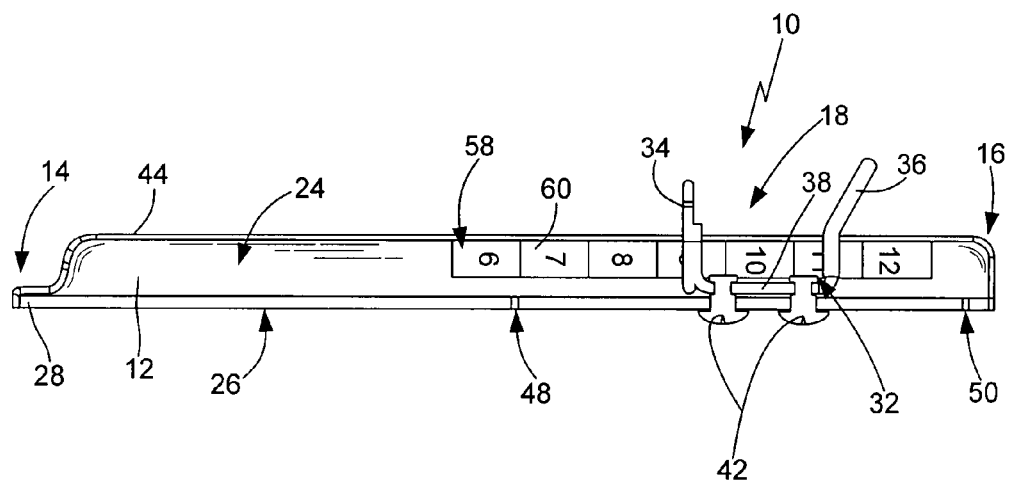
FIG. 4 is a sectional side view of the canine leg measurement device of FIG. 3 taken through lines 4-4 thereon.

In the configuration shown in the figures, sliding mechanism 18 comprises a slide member 32 that is configured to slidably engage the body member 12 such that slide member 32 moves generally along a portion of body member 12, as shown in FIGS. 1 and 2. Various configurations can be utilized for slide member 32 and its slidable engagement with body member 12. In the embodiment shown, slide member 32 has a forward facing, meaning generally towards first end 14, contact plate 34 that is configured to abut the front leg 20 of dog 22 and a rearward facing, meaning generally towards second end 16, push plate 36 that is configured to be pushed by the user. Contact plate 34 and push plate 36 are interconnected by base member 38. In the preferred configuration, these components of slide member 32 are integrally formed. As shown in the figures, both contact plate 34 and push plate 36 extend upwardly from base member 38, which contacts upper surface 24 in a manner that allows it to slide in relation thereto. In this configuration, slide member 32 will move along at least a portion of body member 12 with the upwardly extending contact plate 34 being pushed against the front leg 20 of dog 22 to obtain the desired measurement. Preferably, contact plate 34 is generally perpendicular to base member 38 so that it provides a generally flat surface to abut the front leg 20 and push plate 36 is curved rearwardly towards the second end 16 of body member 12 so as to provide a surface that is easy for the user's thumb to push or pull against to slide the slide member 32 forward or rearward during use of leg measurement device 10. As described below, contact plate 34 of slide member 32 is utilized to obtain a measurement reading from leg measurement device 10 that is then utilized to set the height of a jump apparatus (not shown), such as the hurdles utilized in Flyball competitions or the like.

Slide member 32 can slidably attach to body member 12 in a variety of configurations that are generally well known to those skilled in the art. In the preferred embodiment of the present invention, slide mechanism 18 further comprises an elongated slot 40 and one or more fasteners 42 that slidably attach slide member 32 to body member 12 through slot 40, as described below. In the preferred configuration, slot 40 is disposed in body member 12 at or near the center of its width (i.e., between first edge 44 and second edge 46 of body member 12) and positioned generally toward the second end 16 thereof, as best shown in FIG. 5. Slot 40 has a first end 48 at or in the direction of first end 14 of body member 12 and a second end 50 that is at or near the second end 16 of body member 12. In use, slide member 32 will be configured to generally slide between the first end 48 and second end 50 of slot 40 to obtain the desired measurement. As shown, it is generally not necessary for the first end 48 of slot 40 to extend all of the way to first end 14 of body member 12, as such small measurements are typically not necessary for the use of the leg measurement device 10 to measure the desired length on a dog 22. Likewise, if desired the second end 16 of body member 12 can extend rearwardly of the second end 50 of slot 40 to provide more of a "handle" gripping section.

In one preferred configuration of sliding mechanism 18, fasteners 42 have a base section 52 and an upwardly protruding section 54, as best shown in FIG. 5. The upwardly protruding section 54 is sized and configured to engage an aperture 56 in the base member 38 of slide member 32, by extending upward through slot 40 with base section 52 generally abutting the lower surface 26 of body member 12, in a manner that allows slide member 32 to slide relative to the upper surface 24 of body member 12. During use, base section 52 will slide against and relative to the lower surface 26 of body member 12. The resistance to the ability of slide member 32 to slide relative to body member 12 can be varied by the "clamping" or "gripping" effect of fasteners 42 with slide member 32. Preferably, slide member 32 is configured to slide along body member 12 without requiring a significant amount of force by the user, but with enough resistance that it will not easily slide when the user removes his or her hand therefrom. In this manner, the measuring positioned will be held in place when the user moves leg measurement device 10 away from the dog 22.

To simplify obtaining the desired measurement from the front leg 20 of dog 22, the preferred configuration of leg measurement device 10 includes at least one measurement chart 58 disposed on the upper surface 24 of body member 12. Although the desired measurement could be obtained without the use of a measurement chart 58 on body member 12, for instance by measuring the distance between outwardly extending end 30 and contact plate 34 using a ruler, tape measure or other measuring device, the use of measurement chart 58 allows the user to directly obtain the desired measurement without having to use a second measuring device. In a preferred embodiment, as best shown in FIGS. 1 through 3 and 5, leg measurement device 10 has a pair of measurement charts 58 placed on upper surface 24 at or near the first 44 and second 46 edges of body member 12. The measurement charts 58 can be stickers that are placed on upper surface 24 or be engraved, imprinted, printed or otherwise be part of upper surface 24. Preferably, relatively narrow and elongated measurement charts 58, as shown, are utilized so as to not interfere with the movement of slide member 32 in slot 40. Typically, it is only necessary for the measurement chart 58 to extend between the first 48 and second 50 ends of slot 40.

Figures 8, 9:
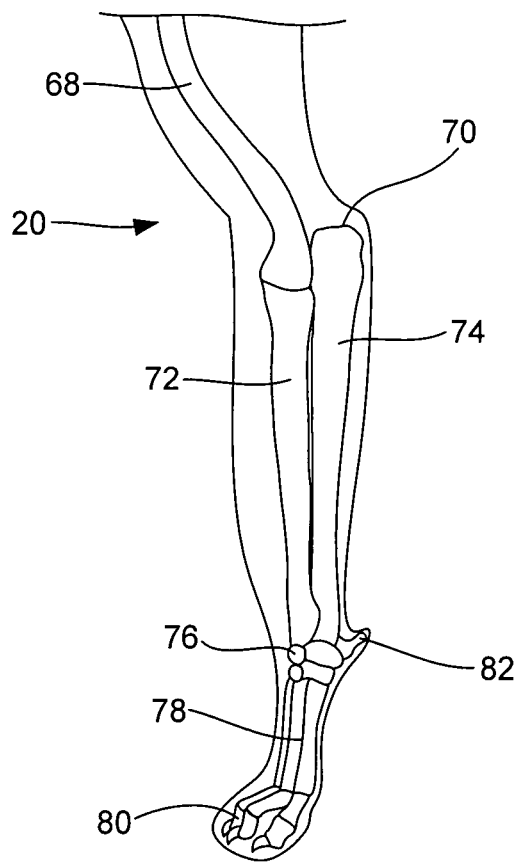
FIG. 8 is a side view of a front leg of a dog showing the portion thereof that is measured with the canine leg measurement device of the present invention.
FIG. 9 is a table correlating the measurement obtained with the canine leg measurement device of the present invention to a jump height setting that is used to set the height of a jump apparatus.

In one embodiment, measurement charts 58 can display the actual distance from outwardly extending end 30 to a point on the measurement chart 58 measured in inches, centimeters and/or millimeters. The user would then have to use the actual measurements to calculate or otherwise determine the height at which the jump apparatuses need to be set. To avoid this extra step, however, the preferred embodiment of measurement charts 58 has a plurality of display panels 60 thereon that correspond to the height setting of the jump apparatus that is required due to the length that is measured by leg measurement device 10. For instance, instead of displaying the actual distance in inches from the outwardly extending end 30, the embodiment shown in the figures displays the jump height setting in display panels 60 that results from the measurement of the front leg 20 of dog 22. For ease of use, it is preferred that the display panels 60 be colored coded such that the different height settings have different colors. The numbers displayed in display panels 60 of the embodiment shown in the figures are based on the measurement table 62 set forth in FIG. 9. If desired, the same color coding can be used for measurement table 62 as for measurement chart 58. Measurement table 62 sets forth the correlation between the measured distance, shown as 64, and the jump height setting, shown as 66, that is used to set the height of the jump apparatuses for a preferred embodiment of using the leg measurement device 10 of the present invention. As explained below, the data correlation shown in FIG. 9 are believed to provide a fairer balance between a dog's jumping ability and the height which the dog 22 must jump than the current method of measuring dog 22 at its withers using a wicket device. As will be readily understood in the art, other correlation data can be used for measurement table 62 by adjusting the relationship between the measured distance 64 and the jump height setting 66. In addition, if desired instead of using a pair of measurement charts 58 that both have display panels 60 with jump height settings 66 thereon, one of the measurement charts 58 can display the length in inches or other units of measure.

Though not shown, leg measurement device 10 of the present invention can also be provided with locking mechanism that locks slide member 32 in place once the measurement is obtained. If desired, the locking mechanism can be incorporated into the sliding mechanism 18 in a manner that is generally known by those skilled in the art. With such a locking mechanism, the user could move slide member 32 along body member 12 until the measurement is achieved and then engage the locking mechanism to lock slide member 32 in position. In this manner, when the user moves the leg measurement device 10 away from dog 22 the measurement will remain in a fixed position.

The use of leg measurement device 10 is shown in FIGS. 6 and 7, the relevant anatomy of dog 22 is shown in FIG. 8 and the measurement chart 62 is shown in FIG. 9. As set forth in FIG. 8, front leg 20 of dog 22 comprises a humerus 68 that connects the shoulder (not shown) to the elbow 70, a partially fused radius 72 and ulna 74 that connects the elbow 70 to the carpus 76, and a metacarpus 78 that connects the carpus 76 to the bones that make up paw 80. Just above the stop or carpal pad (not specifically identified) is the protruding accessory carpal bone (pisiform) 82. The inventor has found that measuring the ulna 74 portion of the front leg 20 between the elbow 70 and the intersection of the ulna 74 and the accessory carpal bone 82, which does not vary in length at maturity, provides a more consistent and accurate measurement than measuring at the withers. In addition, the method of measuring the ulna 74 provides a more equitable measurement for all dogs regardless of their body style (i.e., does not penalize heavy bodied dogs). By taking into account the actual length of a portion of the dog's leg, the heavier bodied dogs are not required to jump disproportionate jump heights.

In use, the dog's handler places the dog in the position shown in FIG. 6 with the front leg 20 presented and the paw 80 in a relaxed position. The inventor has found that this particular stance is easiest and most consistent way of obtaining the desired measurement. The judge 84, the hand of whom is shown in FIGS. 6 and 7, positions the leg measurement device 10 by cradling the front leg 20 into the curved upper surface 24 of body member 12, with ulna 74 abutting the upper surface 24, and then places the outwardly extending end 30 of tip 28 lightly against the intersection of the ulna 74 and the protruding accessory carpal bone 82. The outwardly extending tip 30 is curved, as shown in the figures, to provide a better contact surface against the dog 22 than if it was straight. Using his or her thumb, the judge 84 pushes against push plate 36 to move the slide member 32 along body member 12, with the upwardly protruding section 54 of fasteners 42 inside slot 40, until the contact plate 34 snugly abuts the dog's elbow 70. Once the proper placement has been made, the leg measurement device 10 is removed from the dog 22 and the jump height setting 66 is read and recorded. In use with Flyball, this number is utilized to set the height of the hurdles or in other sports the various jump apparatuses over which the dog 22 must jump to complete its task. The time required to obtain the necessary measurement utilizing the leg measurement device 10 is typically thirty seconds or less, which is somewhat less time than is usually required to measure the withers with a wicket type of device. Naturally, this results in much less stress for the dog, the handler and the judge.

For use in measuring dogs, the leg measurement device 10 can be configured as a hand-held tool with the incremental color coded display panels 60 configured to quickly and easily provide the jump height setting 66 for a range of measurement distances 64, as shown on the measurement table 62. Being hand-held, the leg measurement device 10 is easier to handle and transport than most devices used for measuring withers. As will be readily appreciated by those skilled in the art, depending on the materials used, the leg measurement device 10 is relatively inexpensive to manufacture. More importantly, however, the leg measurement device 10 and the method of determining a jump height setting described herein provides a more consistent and fair way of determining the height the dog 22 should be expected to jump in dog sporting activities such as Flyball and the like. This greatly reduces potential controversy in measurement, thereby providing a more pleasurable environment for the dog sporting event.

While there are shown and described herein specific forms of the invention, it will be readily apparent to those skilled in the art that the invention is not so limited, but is susceptible to various modifications and rearrangements in design and materials without departing from the spirit and scope of the invention. In particular, it should be noted that the present invention is subject to a number modification with regard to any dimensional relationships set forth herein and modifications in assembly, materials, size, shape, and use. For instance, there are numerous components described herein that can be replaced with equivalent functioning components to accomplish the objectives of the present invention.

What is claimed is:

1. A leg measurement device for measuring a leg of an animal, said leg measurement device comprising:
   a body member having a first end, a second end, an upper surface and a lower surface, said first end having a tip with an outwardly extending end that extends outwardly from said first end of said body member, said outwardly extending end configured to abut an accessory carpal bone of the leg;
   a sliding mechanism slidably attached to said body member, said sliding mechanism having a slide member configured to slide on said body member; and
   at least one measurement chart on said body member, said measurement chart configured to determine a jump height setting when a portion of the leg is disposed between said first end of said body member and said sliding mechanism.

2. The leg measurement device according to claim 1, wherein said slide member comprises a contact plate, a push plate and a base member interconnecting said contact plate and said push plate, said base member configured to slide in relation to said upper surface of said body member.

3. The leg measurement device according to claim 1, wherein said body member has a generally curved cross-section.

4. The leg measurement device according to claim 1, wherein said sliding mechanism further comprises a slot disposed in said body member, said slide member slidably engaging said slot.

5. The leg measurement device according to claim 4, wherein said sliding mechanism further comprises one or more fasteners configured to slidably attach said slide member to said body member through said slot.

6. The leg measurement device according to claim 4, wherein said slide member comprises a contact plate, a push plate and a base member interconnecting said contact plate and said push plate, said base member configured to slide in relation to said upper surface of said body member.

7. The leg measurement device according to claim 6, wherein said contact plate extends upwardly from said base member so as to contact the leg when said slide member is slid toward said first end of said body member.

8. The leg measurement device according to claim 1, wherein said measurement chart directly provides said jump height setting.

9. A leg measurement device for measuring a leg of an animal, said leg measurement device comprising:
an elongated body member having a first end, a second end, an upper surface and a lower surface, said body member having a generally curved cross-section;
a tip at said first end of said body member;
a sliding mechanism slidably attached to said body member, said sliding mechanism having a slot disposed in said body member and a slide member slidably engaging said slot; and
at least one measurement chart on said body member, wherein said leg measurement device measures the distance between an accessory carpal bone and an elbow of the leg to provide a jump height setting from said measurement chart when said upper surface of said body member is placed against an ulna of the leg, said tip engages the leg at the accessory carpal bone and said sliding mechanism abuts the elbow.

10. The leg measurement device according to claim 9, wherein said tip has an outwardly extending end that extends outwardly from said first end of said body member, said outwardly extending end configured to abut the accessory carpal bone of the leg.

11. The leg measurement device according to claim 9, wherein said sliding mechanism further comprises one or more fasteners configured to slidably attach said slide member to said body member through said slot.

12. The leg measurement device according to claim 9, wherein said slide member comprises a contact plate, a push plate and a base member interconnecting said contact plate and said push plate, said base member configured to slide in relation to said upper surface of said body member.

13. The leg measurement device according to claim 12, wherein said contact plate extends upwardly from said base member so as to contact the elbow of the leg when said slide member is slid toward said first end of said body member.

14. A method of measuring a leg of an animal with a leg measurement device to determine a jump height setting, said method comprising the steps of:
a) positioning the animal with the leg presented and the paw relaxed;
b) supporting the leg against an upper surface of a body member of said leg measurement device;
c) placing a first end of said body member against the intersection of an ulna and an accessory carpal bone of the leg;
d) sliding a slide member toward said first end of said body member until it abuts an elbow of the leg, said slide member slidably attached to said body member of said leg measurement device; and
e) reading a measurement chart on said upper surface where said slide member abuts the elbow to determine said jump height setting.

15. The method of claim 14, wherein said body member has curved cross-section and the leg is cradled by said body member in said supporting step.

16. The method of claim 14, wherein said first end of said body member has a tip with an outwardly extending end that engages the intersection of the ulna and the accessory carpal bone of the leg.

17. The method of claim 14, wherein said slide member slidably engages a slot disposed in said body member and said slide member has a contact plate that abuts the elbow.

18. The method of claim 14, wherein said measurement chart directly indicates said jump height setting.

* * * * *